(12) United States Patent
Hunt

(10) Patent No.: US 10,286,121 B2
(45) Date of Patent: May 14, 2019

(54) DEVICE FOR DRAWING AND EXPELLING A LIQUID OR POWDER

(71) Applicant: Ulus Landon Hunt, Denton, TX (US)

(72) Inventor: Ulus Landon Hunt, Denton, TX (US)

(*) Notice: Subject to any disclaimer, the term of this patent is extended or adjusted under 35 U.S.C. 154(b) by 0 days.

(21) Appl. No.: 15/482,900

(22) Filed: Apr. 10, 2017

(65) Prior Publication Data

US 2018/0085503 A1 Mar. 29, 2018

Related U.S. Application Data

(60) Provisional application No. 62/320,721, filed on Apr. 11, 2016.

(51) Int. Cl.
| | |
|---|---|
| *A61M 1/00* | (2006.01) |
| *A47J 37/10* | (2006.01) |
| *B65D 35/38* | (2006.01) |
| *B65D 1/32* | (2006.01) |
| *B65D 83/06* | (2006.01) |
| *B65D 43/02* | (2006.01) |
| *B65D 35/08* | (2006.01) |
| *B65D 25/48* | (2006.01) |
| *B65D 83/00* | (2006.01) |
| *B65D 45/32* | (2006.01) |
| *A61M 31/00* | (2006.01) |

(52) U.S. Cl.
CPC .......... *A61M 1/0003* (2013.01); *A47J 37/106* (2013.01); *B65D 1/32* (2013.01); *B65D 25/48* (2013.01); *B65D 35/08* (2013.01); *B65D 35/38* (2013.01); *B65D 43/0225* (2013.01); *B65D 45/325* (2013.01); *B65D 83/0055* (2013.01); *B65D 83/06* (2013.01); *A61M 31/00* (2013.01); *A61M 2202/064* (2013.01); *A61M 2205/0216* (2013.01); *A61M 2210/0618* (2013.01)

(58) Field of Classification Search
CPC ........ A61M 3/0262; A61M 2210/1475; A61M 1/003
USPC .......................................... 604/12
See application file for complete search history.

(56) References Cited

U.S. PATENT DOCUMENTS

| | | | | |
|---|---|---|---|---|
| 1,961,489 A | * | 6/1934 | Hein .................. | A61M 5/2425 15/405 |
| 4,258,714 A | * | 3/1981 | Leopoldi ............ | A61M 3/0262 604/118 |
| 5,758,802 A | * | 6/1998 | Wallays ............... | A21C 15/005 222/212 |
| 5,848,993 A | * | 12/1998 | Tanhehco ............ | A61M 1/0011 604/217 |
| 8,348,906 B2 | | 1/2013 | Tanaka et al. | |

(Continued)

*Primary Examiner* — Nathan R Price
*Assistant Examiner* — John A Doubrava
(74) *Attorney, Agent, or Firm* — Sheri Higgins Law; Sheri Higgins

(57) ABSTRACT

A device includes: a base; and an applicator tip, wherein the base and applicator tip are removably connected to each other via a connection, and wherein the device draws and expels a liquid or powder by alternating an increase and decrease of pressure within the device. The device can be used as a nasal aspirator, applicator, or baster for food products. The applicator tip and base can be removably connected to each other via a threaded connection or snap-fit connection. Force applied to the base decreases the volume of the base to create a pressure differential to draw and expel the liquid or powder from the device.

20 Claims, 3 Drawing Sheets

(56) References Cited

U.S. PATENT DOCUMENTS

| | | | |
|---|---|---|---|
| 2007/0038177 A1* | 2/2007 | Sinha | A61M 25/02 |
| | | | 604/96.01 |
| 2009/0209936 A1* | 8/2009 | Tanaka | A61K 9/007 |
| | | | 604/500 |

* cited by examiner

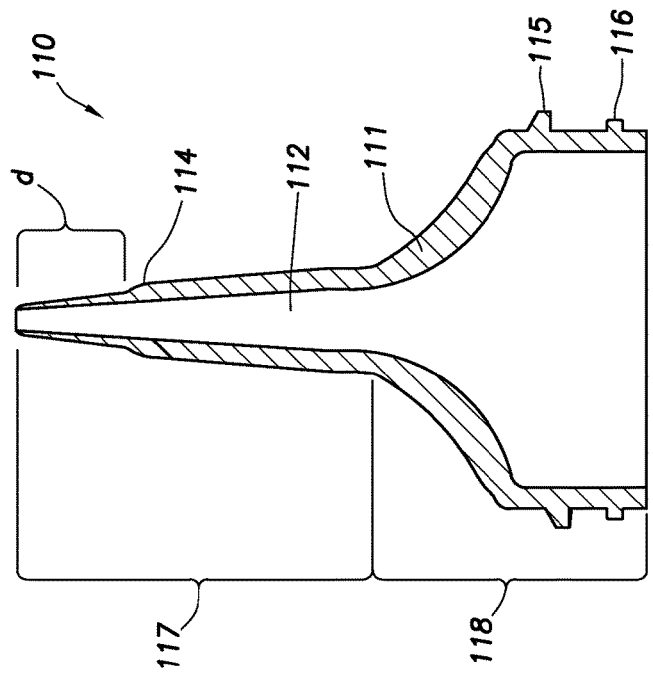
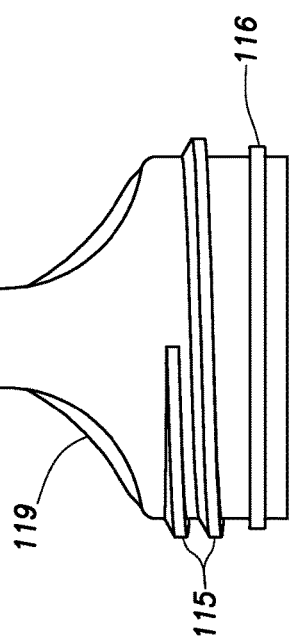
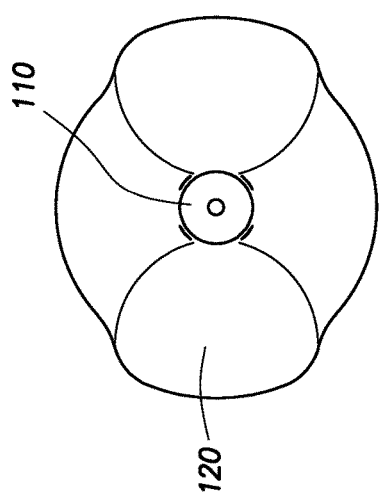

DEVICE FOR DRAWING AND EXPELLING A LIQUID OR POWDER

TECHNICAL FIELD

Devices that can draw or suck and expel a liquid or powder are used in a variety of applications, including nasal aspirators, basters for food products, and application of powders.

BRIEF DESCRIPTION OF THE FIGURES

The features and advantages of certain embodiments will be more readily appreciated when considered in conjunction with the accompanying figures. The figures are not to be construed as limiting any of the preferred embodiments.

FIG. 3 is a top perspective view of the device of FIG. 1.

FIG. 4 is a cross-sectional view of an applicator tip showing various components according to certain embodiments.

FIG. 5 is a perspective view of the applicator tip of FIG. 4.

DETAILED DESCRIPTION

Many industries sell devices that can draw and expel a liquid or a powder for a variety of applications. Such applications include, but are not limited to: nasal aspirators for infants, children, and adults; basters for food products; and applicators for powders, such as baby powder. However, such devices can generally be difficult to clean properly-resulting in a risk of bacterial growth, which can contaminate a food product or infect a person. The devices can also generally be difficult to operate-resulting in inadequate drawing and/or expelling capabilities. As such, there is a need for an improved device for drawing and expelling a liquid or powder.

It has been discovered that a suction device for drawing and expelling a liquid or powder can include detachable components. The components can be easily assembled for use. After use, the components can be disassembled, which allows the components to be cleaned and/or sanitized before the next use. The cleaning and/or sanitization can reduce or eliminate the risk of bacterial infection to people.

According to certain embodiments, a suction device comprises: a base; and an applicator tip, wherein the base and applicator tip are removably connected to each other via a connection, and wherein the device draws and expels a liquid or powder by alternating an increase and decrease of pressure within the device.

Figure 1:
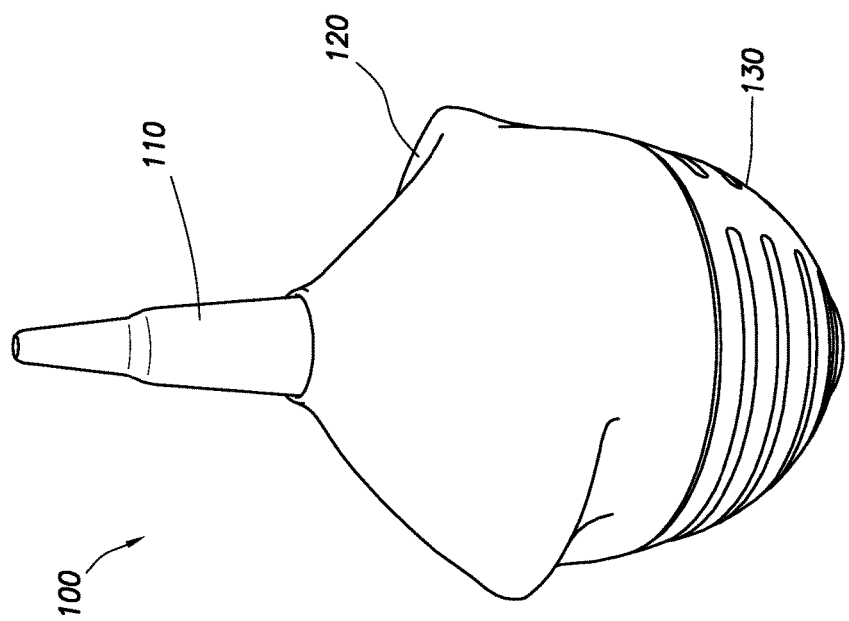
FIG. 1 is a perspective view of a device for drawing and expelling a liquid or powder according to certain embodiments.

Turning to the figures, FIG. 1 is a perspective view of a suction device 100 for drawing and expelling a liquid or powder. As used herein, a "liquid" is a fluid having a continuous phase that tends to flow and to conform to the outline of its container when the fluid is tested at a temperature of 71° F. (22° C.) and a pressure of 1 atmosphere "atm" (0.1 megapascals "MPa"). As used herein, a "powder" means fine dry particles that can be produced by the grinding, crushing, or disintegration of a solid substance. The particle size of the powder can vary and can range from about 5 micrometers (μm) to about 2.5 millimeters (mm). The liquid can also contain soluble compounds and insoluble materials. For a food product, for example, a liquid from a turkey can also include liquid water, juices from the turkey, insoluble herbs, insoluble vegetables, such as onions and carrots, and combinations thereof.

Figure 2:
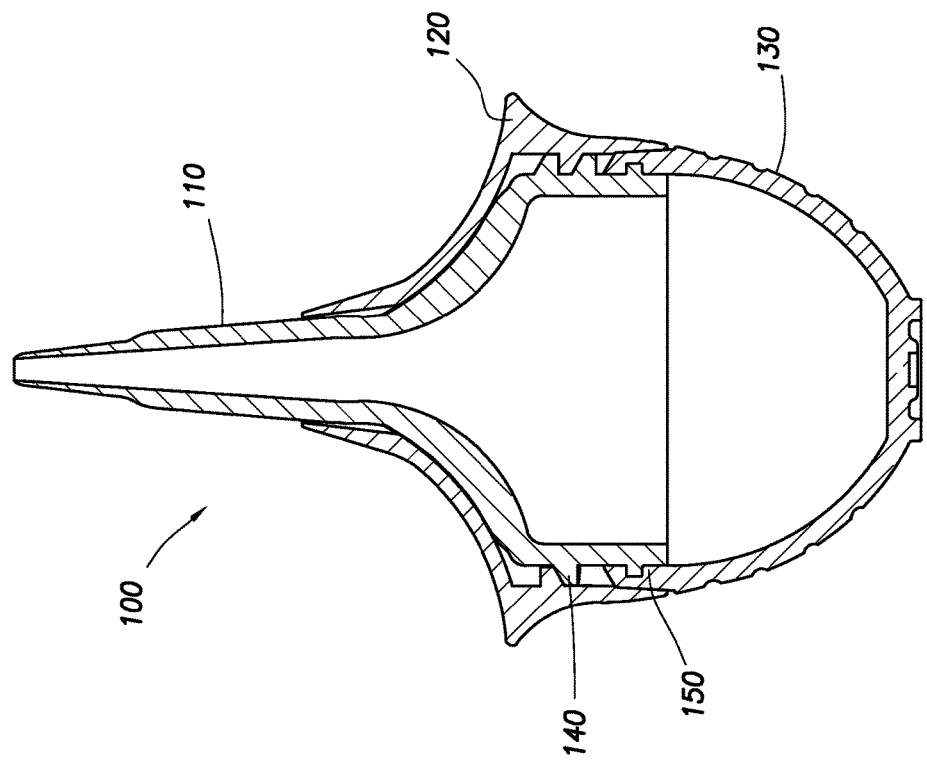
FIG. 2 is a cross-sectional view of the device of FIG. 1 showing various components according to certain embodiments.

The device 100 can include a base 130 and an applicator tip 110. According to certain embodiments, the device 100 further includes a cover 120. FIG. 2 is a cross-sectional view of the device 100 showing a first connection 140 and a second connection 150. The first connection 140 can connect the applicator tip 110 and the cover 120. The second connection 150 can connect the applicator tip 110 and the base 130. As will be discussed below in more detail, the first connection 140 and second connection 150 are non-permanent connections. In this manner, the components of the device 100 can be assembled or connected to one another for use and then disassembled or disconnected from one another for cleaning.

FIG. 3 is a top perspective view of the device 100 showing a portion of the applicator tip 110 being positioned through an opening at the top of the cover 120.

As shown in FIGS. 4 and 5, the device 100 includes the applicator tip 110. The applicator tip 110 can include sidewalls 111 that form a cavity within the applicator tip 110. The cavity can include a passageway 112 for flow of the liquid or powder. The top of the applicator tip 110 includes an opening 113. The opening 113 allows the liquid or powder to be drawn into or expelled from the passageway 112.

As shown, the applicator tip 110 can include a stem portion 117 and a body portion 118. The stem portion 117 can have a smaller outer diameter (OD) than the body portion 118. The stem portion 117 can include the passageway 112 and the body portion 118 can include the cavity. The stem portion 117 can also be tapered from a lower end of the stem portion 117 to a top end of the stem portion 117 where the opening 113 is located. A smaller OD of the stem portion 117 as well as tapering of the stem portion 117 can be useful when the device 100 is used as a nasal aspirator. It is to be understood that the applicator tip 110 can only include the body portion 118. According to this embodiment, the applicator tip 110 can have a uniform OD from a bottom to a top of the applicator tip 110. The body portion 118 can also be tapered from the bottom to the top of the applicator tip 110. This embodiment can be useful when the device 100 is used as a baster for food products or the application of medicinal or non-medicinal liquids or powders. The body portion 118 can include the passageway 112.

For use as a nasal aspirator, the stem portion 117 can also include a safety protrusion 114. The safety protrusion 114 can have a larger OD than the top of the stem portion 117. The safety protrusion 114 can inhibit or prevent injury or damage to a person when using the device 100 as a nasal aspirator by coming in contact with the soft tissue forming the nostrils and halting upward movement of the top of the applicator tip 110 into the nostril. The safety protrusion 114 can be located a distance d from the opening 113 of the applicator tip 110. The distance d can vary and be selected based, in part, on whether the nasal aspirator is to be used for an infant, toddler, teenager, or adult. For example, the distance d will generally be less for an infant nasal aspirator compared to an adult nasal aspirator. The distance d can be in the range from about 0.75 centimeters (cm) to about 2.5 cm.

The applicator tip 110 can include outer threads 115 and/or a flange 116. The outer threads 115 and/or the flange 116 can be located at or near the bottom of the applicator tip 110. The outer threads 115 and/or the flange 116 can be used to connect and disconnect the applicator tip 110 to the base 130. If the device 100 also includes the cover 120, then there can be more than one of the outer threads 115 and/or flange 116. One set of threads or flange can be used to connect and disconnect the applicator tip 110 to the base 130 and another set of threads or flange can be used to connect and disconnect the applicator tip 110 to the cover 120. The outer threads 115 can be circumferentially positioned in a spiral pattern around and protrude from the sidewalls 111 of the applicator tip 110. The number of threads can vary and can range from about 2 to about 5. The flange 116 can be circumferentially positioned around and protrude from the sidewalls of the applicator tip 110. There can also be more than one flange.

According to certain embodiments, the applicator tip 110 further includes one or more ridges 119 on a top of the body portion 118. The ridges 119 can be arranged like spokes radiating out toward a perimeter from a central point on the top of the body portion 118. The length, height, and spacing of the ridges 119 can be selected such that when the applicator tip 110 includes outer threads 115, the ridges 119 prevent over tightening during assembly or connection.

The applicator tip 110 can be made from a variety of materials. The material can be a resilient material that provides a pliable interface for contacting sensitive surfaces, such as in a nasal cavity or passage or a semi-rigid or rigid material. The material can be transparent or opaque. Resilience is the ability of a material to absorb energy when it is deformed elastically, and release that energy upon unloading. Examples of resilient materials include, but are not limited to, flexible plastics, rubbers, and elastomers. The rubber can be a latex-free rubber. Examples of semi-rigid to rigid materials include, but are not limited to, thermoplastics, plastics, metals, metal alloys, and glass. A resilient material may be best suited for nasal aspirator applications while semi-rigid to rigid materials may be best suited for basters or applicators. For a baster, the applicator tip 110 can also include a covering at the top of the applicator. The covering can be made of a different material than the applicator tip 110. By way of example, if the applicator tip 110 is made from glass, then the covering can be made from a metal. The covering can protect the applicator tip 110 from excessive heat or a force during use as a baster. Preferably, any of the materials for forming the device 100 are heat resistant and have a melting point that is higher than water in a dishwasher or liquid from a food product being cooked. In this manner, degradation or deformation from heat is prevented.

The dimensions of the applicator tip 110 can vary based on the specific application. The length of the applicator tip 110 can range from about 2 inches (in) to about 8 in. The outer diameter of the applicator tip 110 can range from about 1.5 in to about 4 in. As discussed above, the OD can taper and as such, the OD can also vary, wherein the largest OD is in the stated range. For a nasal aspirator, the top of the applicator tip 110 can have an OD that is sufficient to allow the top of the applicator tip 110 to be positioned within a nasal cavity via a nostril. According to this embodiment, the OD at the top of the applicator tip 110 can be in the range of about 0.2 in to about 0.5 in.

Figure 9:
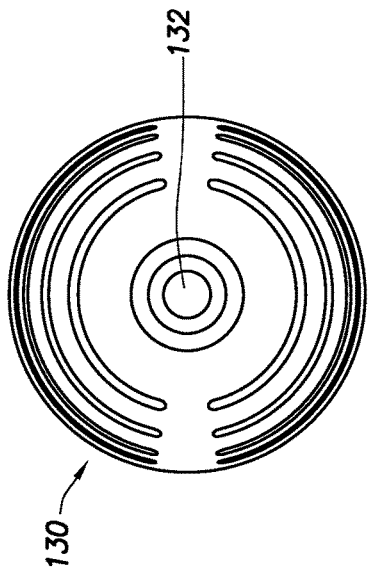
FIG. 9 is a bottom perspective view of the base.
Figure 8:
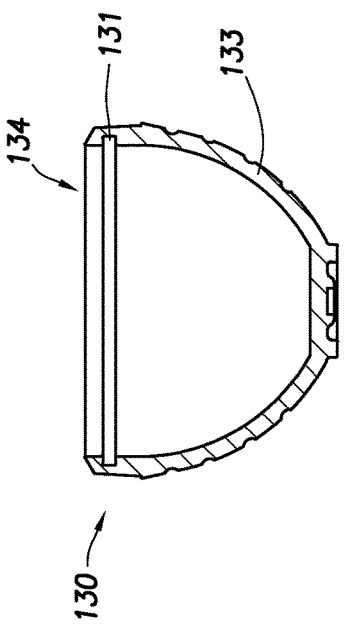
FIG. 8 is a cross-sectional view of a base showing various components according to certain embodiments.

The device 100 also includes the base 130. As shown in FIGS. 8 and 9, the base 130 can have a generally circular cross-sectional shape. The base 130 can include sidewalls 133 that form a cavity 134 within the base 130.

The base 130 and the applicator tip 110 can include a second connection 150 for the base and applicator tip. The second connection 150 can be used to disassemble and assemble the base and the applicator tip. In this manner, proper cleaning of the base and applicator tip can be easily accomplished. The second connection 150 can be a threaded connection or a pressure connection, such as a snap-fit connection. The base 130 can include one or more recesses or inner threads 131 (shown in FIG. 8 as one recess) located at or near the top of the base 130. The one or more recesses 131 can mate with and receive a flange 116 of the applicator tip 110 for assembly and connection or disassembly and disconnection of the base and applicator tip. Preferably, the dimensions and location of the one or more recesses are selected such that one or more flanges can fit within and mate with the recess. This mating engagement can ensure a tight connection of the base and applicator tip to provide improved drawing or sucking capability of the device. Inner threads 131 can be used to conjoin with outer threads 115 of the applicator tip 110 for assembly and connection or disassembly and disconnection of the base and applicator tip. According to certain embodiments, the base 130 is connected to the applicator tip 110 via a recess 131 on the base and a flange 116 on the applicator tip 110 by applying a force to the base and applicator tip in a non-opposing direction to create a snap-fit connection. According to certain embodiments, the connection is designed such that air is inhibited or prevented from escaping from the base/applicator tip assembly during use. This can aid in obtaining adequate suction during use.

In practice and after assembly of the base 130 with the applicator tip 110, a force is applied to the bottom of the base, for example via a thumb positioned on an actuation area 132, to move the bottom of the base towards the opening 113 in the applicator tip 110. A force can also be applied to the base 130 by squeezing the sidewalls 133 toward each other at the sides of the base. The movement of the bottom or sidewalls of the base reduces the volume within the device to provide a pressure differential between the inside and outside of the device. The applicator tip 110 can then be inserted into an object containing a liquid or powder. The force being applied to the bottom of the base 130 can then be removed, which draws or sucks the liquid or powder through the opening 113, through the passageway 112, and into the cavity 134 of the base 130. It is to be understood that the liquid or powder can completely fill the cavity 134 and some of the liquid or powder can remain in the cavity of the body portion 118 and/or the passageway 112 of the applicator tip 110. This embodiment may occur when the device 100 is used as a baster. The applicator tip 110 can then be removed from the object, and the force can be re-applied to the bottom or sidewalls of the base in order to expel the liquid or powder from the device.

According to certain embodiments, the base 130 is made from a resilient material that allows flexing to create pressure variations in the device by varying the volume within the base. The base can be made from a variety of materials, including but not limited to, flexible plastics, rubbers, and elastomers. The rubber can be a latex-free rubber.

The base 130 can have a variety of dimensions. For example, depending on the intended application, the outer diameter of the base 130 may be smaller for an infant nasal aspirator and larger for a baster. The OD of the base 130 can range from about 1.5 in to about 4 in. The base 130 can be bowl-shaped or conical-shaped. As such, the OD of the base 130 can taper, wherein the largest OD is in the stated range. The base 130 can have a height ranging from about 1.5 in to about 6 in. The dimensions of the base 130 and the applicator tip 110 can be selected to provide a desired total volume of the device 100. The desired volume of the cavity 134 and passageway 112 can range from about 20 milliliters (mL) to about 350 mL—depending in part on the type of application the device is used for (i.e., nasal aspirator or baster).

Figure 7:
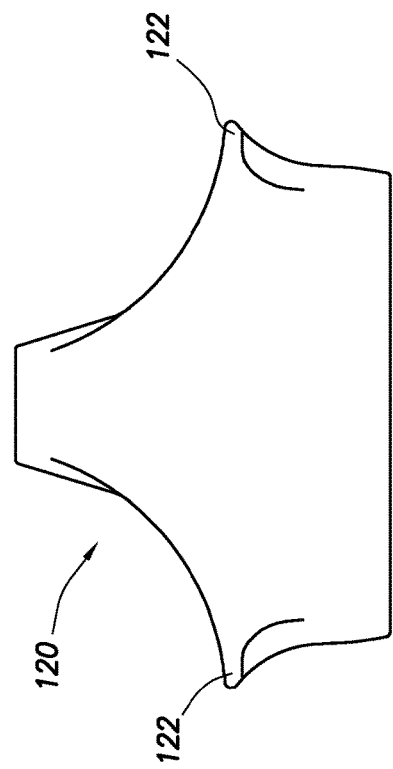
FIG. 7 is a front perspective view of a portion of the cover.
Figure 6:
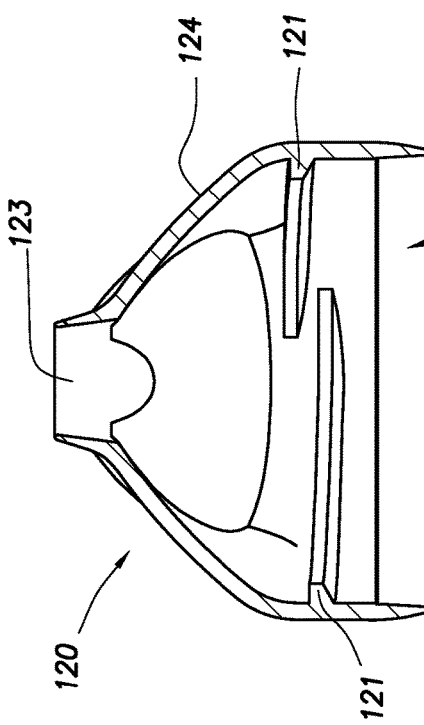
FIG. 6 is a cross-sectional view of a portion of a cover showing various components according to certain embodiments.

As shown in FIGS. 6 and 7, the device 100 can further include a cover 120. The cover 120 can encompass a portion of the base 130 and the applicator tip 110, for example, as shown in FIGS. 1 and 2. The cover 120 can include a pass through 123, which is an opening in the top of the cover, for placing the cover over the stem portion 117 and/or body portion 118 of the applicator tip 110. The cover 120 includes sidewalls 124 that form the cover and a cavity 125 within the cover. The cavity 125 allows the cover 120 to be positioned over the base 130 and the applicator tip 110.

The cover 120 can be installed over the applicator tip 110 and removably attached to the applicator tip 110 via a first connection 140. The first connection 140 can be a threaded connection or pressure connection, such as a snap-fit connection. As shown in FIG. 6, the cover 120 can include inner threads 121. The inner threads 121 can be spirally positioned around an inner diameter of the cover 120. The inner threads 121 can be threaded onto outer threads 115 on the applicator tip 110. For a pressure connection, the first connection 140 can include a flange 116 on the outside of the applicator tip 110 and a recess on the inside of the cover 120. Application of a force causes the flange to fit within and mate with the recess; thereby creating a secure connection of the cover 120 with the applicator tip 110. After connection, a bottom portion of the cover 120 can surround a top portion of the base 130.

As shown in FIG. 7, the cover 120 can further include one or more protrusions 122 that extend from an outer perimeter of the cover. The protrusions 122 can be spaced opposite of each other on the cover 120. The protrusions 122 can include a concave area. The concave area on each protrusion can create an area for a user's fingers to be positioned during use of the device 100. This embodiment is especially useful when the force for drawing and expelling the liquid or powder is applied to the bottom of the base 130, for example, via pressure on the actuation area 132 of the base 130. The protrusions can provide an improved gripping surface for the user or for the user's fingers. The protrusions can also aid in providing increased suction during use.

The cover 120 can be made from a variety of materials. The material can be a resilient material that provides a pliable interface for placing the cover over the base and the applicator tip. Examples of resilient materials include, but are not limited to, flexible plastics, rubbers, and elastomers. By covering a portion of the base 130, the applicator tip 110, and the second connection 150, a better suction can be created due to the reduction in loss of air or pressure differentials between the inside and outside of the device 100.

The device 100 can be manufactured according to any method known to those skilled in the art.

Methods of using the device to draw and expel a liquid or powder can include assembling the applicator tip 110 to the base 130 via the second connection 150. This assembly can include screwing the applicator tip 110 to the base 130 via a threaded connection or pressure fitting the applicator tip 110 to the base 130 via one or more flanges and recesses. The methods can further include assembling the cover 120 over the applicator tip 110 and base 130 via a first connection 140. This assembly can include positioning the cover 120 over the stem portion 117 of the applicator tip 110 and either screwing the cover 120 onto the applicator tip 110 via a threaded connection or pressure fitting the cover 120 to the applicator tip 110 via one or more flanges and recesses. The methods can further include applying a force to the base 130 of the device 100 to decrease the volume within the base and create a negative pressure differential between the inside and outside of the device 100. The application of the force can be removed, wherein removal causes a liquid or powder to flow into the device 100. After entry of the liquid or powder, the force can be re-applied to the base 130 whereby the fluid or powder exits the device 100. The cover 120 can then be disassembled from the base 130 and applicator tip 110 by unscrewing the threaded connection or pulling the cover 120 away from the base 130. The applicator tip 110 can then be disassembled from the base 130 by unscrewing the threaded connection or pulling the applicator tip 110 away from the base 130. The components of the device 100 can then be cleaned and/or sanitized after disassembly.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While devices, systems, and methods are described in terms of "comprising," "containing," or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more connections, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A nasal aspirator device comprising:
a base;
an applicator tip, wherein the base and applicator tip are removably connected to each other via a second connection, wherein the device draws and expels a liquid or powder by alternating an increase and decrease of pressure within the device,
wherein the second connection comprises outer threads located at or near a bottom of the applicator tip and inner threads located at or near a top of the base, and wherein the outer threads conjoin with the inner threads to connect the applicator tip to the base,
wherein the applicator tip further comprises a safety protrusion located near a top of the applicator tip, and wherein the safety protrusion has a fixed larger outer diameter than a portion of the applicator tip located, above the safety protrusion, and wherein the safety protrusion tapers from a larger outer diameter located nearest to the base to a smaller outer diameter located nearest to the top of the applicator tip; and
a cover, wherein the cover is made from a resilient material, wherein the cover encloses a portion of the applicator tip, a portion of the base, and the second connection, wherein the cover comprises sidewalls that form the cover and a cavity within the cover, and wherein the cavity allows the cover to be positioned over the base and the applicator tip, and wherein the cover and applicator tip are removably connected to each other via a first connection.

2. The device according to claim 1, wherein the applicator tip comprises sidewalls that form a cavity within the applicator tip.

3. The device according to claim 2, wherein the cavity comprises a passageway for flow of the liquid or powder.

4. The device according to claim 3, wherein a top of the applicator tip further comprises an opening, wherein the opening allows the liquid or powder to be drawn into or expelled from the passageway.

5. The device according to claim 1, wherein the base comprises sidewalk that form a cavity within the base.

6. The device according to claim 1, wherein a force is applied to the base that reduces the volume within the device to provide a pressure differential between the inside and outside of the device.

7. The device according to claim 6, wherein removal of the force draws the liquid or powder into the device.

8. The device according to claim 7, wherein re-application of the force expels the liquid or powder from the device.

9. The device according to claim 1, wherein the first connection comprises outer threads located at or near a bottom of the applicator tip and inner threads located at or near a top of the cover, and wherein the outer threads conjoin with the inner threads to connect the cover to the applicator tip.

10. The device according to claim 1, wherein the first connection comprises a flange located at or near a bottom of the applicator tip and a recess located at or near a top of the cover, wherein the flange is circumferentially positioned around and protrudes from sidewalls of the applicator tip, and wherein the recess receives and mates with the flange to connect the cover to the applicator tip.

11. The device according to claim 1, wherein the applicator tip and base are made from a resilient material, selected from flexible plastics, rubbers, and elastomers.

12. The device according to claim 1, wherein the base is made from a resilient material selected from flexible plastics, rubbers, and elastomers, and wherein the applicator tip is made from a semi-rigid or rigid material selected from thereto-plastics, plastics, metals, metal alloys, and glass.

13. A nasal aspirator device comprising:
a base;
an applicator tip, wherein the base and applicator tip are removably connected to each other via a second connection, wherein the device draws and expels a liquid or powder by alternating an increase and decrease of pressure within the device,
wherein the second connection comprises a flange located at or near a bottom of the applicator tip and a recess located at or near a top of the base, wherein the flange is circumferentially positioned around and protrudes from sidewalls of the applicator tip, and wherein the recess receives and mates with the flange to connect the applicator tip to the base,
wherein the applicator tip further comprises a safety protrusion located near a top of the applicator tip, and wherein the safety protrusion has a fixed larger outer diameter than a portion of the applicator tip located above the safety protrusion, and wherein the safety protrusion tapers from a larger outer diameter located nearest to the base to a smaller outer diameter located nearest to the top of the applicator tip; and
a cover, wherein the cover is made from a resilient material, wherein the cover encloses a portion of the applicator tip, a portion of the base, and the second connection, wherein the cover comprises sidewalls that form the cover and a cavity within the cover, and wherein the cavity allows the cover to be positioned over the base and the applicator tip, and wherein the cover and applicator tip are removably connected to each other via a first connection.

14. The device according to claim 13, wherein the applicator tip comprises sidewalls that form a cavity within the applicator tip, wherein the cavity comprises a passageway for flow of the liquid or powder, wherein a top of the applicator tip further comprises an opening, and wherein the opening allows the liquid or powder to be drawn into or expelled from the passageway.

15. The device according to claim 13, wherein the base comprises sidewalls that form a cavity within the base.

16. The device according to claim 13, wherein a force is applied to the base that reduces the volume within the device to provide a pressure differential between the inside and outside of the device, wherein removal of the force draws the liquid or powder into the device, and wherein re-application of the force expels the liquid or powder from the device.

17. The device according to claim 13, wherein the first connection comprises outer threads located at or near a bottom of the applicator tip and inner threads located at or near a top of the cover, and wherein the outer threads conjoin with the inner threads to connect the cover to the applicator tip.

18. The device according to claim 13, wherein the first connection comprises a flange located at or near a bottom of the applicator tip and a recess located at or near a top of the cover, wherein the flange is circumferentially positioned around and protrudes from sidewalls of the applicator tip, and wherein the recess receives and mates with the flange to connect the cover to the applicator tip.

19. The device according to claim 13, wherein the applicator tip and base are made from a resilient material selected from flexible plastics, rubbers, and elastomers.

20. The device according to claim 13, wherein the base is made from a resilient material selected from flexible plastics, rubbers, and elastomers, and wherein the applicator tip is made from a semi-rigid or rigid material selected from thereto-plastics, plastics, metals, metal alloys, and glass.

* * * * *